(12) United States Patent
Teoh

(10) Patent No.: US 6,544,275 B1
(45) Date of Patent: Apr. 8, 2003

(54) VASO-OCCLUSIVE COILS WITH SELECTIVELY FLATTENED AREAS

(75) Inventor: Clifford Teoh, Los Altos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 244 days.

(21) Appl. No.: 09/637,714

(22) Filed: Aug. 11, 2000

(51) Int. Cl.⁷ .............................................. A61B 17/08
(52) U.S. Cl. ...................................................... 606/158
(58) Field of Search ................................ 606/191, 200, 606/157, 158, 108; 623/1.22, 1.1, 12.1, 23.69

(56) References Cited

U.S. PATENT DOCUMENTS

| | | |
|---|---|---|
| 4,994,069 A | 2/1991 | Ritchart et al. |
| 5,122,136 A | 6/1992 | Guglielmi et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford et al. |
| 5,312,415 A | 5/1994 | Palermo |
| 5,350,397 A | 9/1994 | Palermo et al. |
| 5,354,295 A | 10/1994 | Guglielmi et al. |
| 5,669,931 A * | 9/1997 | Kupiecki et al. ............ 606/191 |
| 5,690,666 A | 11/1997 | Berenstein et al. |
| 5,766,160 A * | 6/1998 | Samson et al. ................ 606/1 |
| 5,826,587 A | 10/1998 | Berenstein et al. |
| 6,033,423 A * | 3/2000 | Ken et al. .................... 606/191 |
| 6,096,034 A * | 8/2000 | Kupiecki et al. ........... 604/104 |
| 6,143,007 A * | 11/2000 | Mariant et al. ............. 606/151 |
| 6,183,491 B1 * | 2/2001 | Lulo .......................... 606/191 |
| 6,187,027 B1 * | 2/2001 | Mariant et al. ............. 606/151 |
| 6,322,576 B1 * | 11/2001 | Wallace et al. ............. 606/191 |

FOREIGN PATENT DOCUMENTS

| | | |
|---|---|---|
| EP | 0 739 605 | 10/1996 |
| WO | WO 00/35354 | 6/2000 |

* cited by examiner

Primary Examiner—Michael J. Milano
Assistant Examiner—(Jackie) Tan-Uyen T. Ho
(74) Attorney, Agent, or Firm—Robins & Pasternak LLP

(57) ABSTRACT

Vaso-occlusive devices with selectively flattened surfaces are described. Also described are methods of making and using these devices.

14 Claims, 3 Drawing Sheets

VASO-OCCLUSIVE COILS WITH SELECTIVELY FLATTENED AREAS

FIELD OF THE INVENTION

This invention is in the field of an implantable vaso-occlusive device. In particular, the invention includes deployable devices such as coils in which the round wire making up the coil is flattened in at least one area. The coil efficiently self-forms into a three-dimensional shape when deployed into a body cavity. The flattened areas induce the three-dimensional formation in the desired directions and shapes. Methods of producing and using the vaso-occlusive coils are also provided.

BACKGROUND

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration— which is better suited to occlude the vessel—once the device is so placed. Ritchart et al. describes a variety of shapes. The secondary shapes of the disclosed coils include "flower" shapes and double vortices. A random shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

Vaso-occlusive coils having little or no inherent secondary shape have also been described. For instance, co-owned U.S. Pat. Nos. 5,690,666 and 5,826,587 by Berenstein et al., describes coils having little or no shape after introduction into the vascular space.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

None of these documents disclose coils having selectively flattened portions to enhance coil formation in certain directions.

SUMMARY OF THE INVENTION

Thus, this invention includes novel vaso-occlusive devices having flattened surfaces methods of using and making these devices In one aspect, the present invention includes a vaso-occlusive device comprising an elongated wire having a round cross-section wound into a first configuration of a helical linear coil having a longitudinal axis and two ends, wherein the helical linear coil self-forms into a second configuration when deployed into a body cavity and wherein selected portions of the wire wound into the helical linear coil have been flattened such that the cross-section of the wire is not round. The flattened portions allow for efficient coil formation. Thus, the flattened portions of the wire may form a pattern over the longitudinal axis of the coil, for example a striped or helical pattern or, alternatively, may appear to be "random," so long as they are positioned to promote coil formation in the desired directions and shapes. The devices described herein may further include additional filamentary material attached to the coil; a deployment tip (e.g. mechanically or electrolytically detachable ends) attached to at least one of the two ends of the coil.

The selectively flattened devices described herein can be produced, for example, by rolling the linear coil against a high strength material (e.g. mandrel) or by using a swage on the linear coil.

Also included in the present invention is a method of occluding a body cavity comprising introducing any of the vaso-occlusive devices described herein into the body cavity (e.g. an aneurysm).

These and other embodiments of the subject invention will readily occur to those of skill in the art in light of the disclosure herein.

DESCRIPTION OF THE INVENTION

Vaso-occlusive devices, particularly coils, wherein selected areas of the device are flattened are described herein. The flattened areas can be produced in any number of ways, for example by using a swage or by otherwise rolling the primary coil of the device against high strength/hardness material such as a mandrel. Where the coil has been flattened, the resultant cross-section of the wire making up the vaso-occlusive device becomes an ovalized flat circle (e.g., a "D" shape). Methods of making and using these devices also form an aspect of this invention.

Advantages of the present invention include, but are not limited to, (i) more control of three-dimensional shape upon deployment, depending on which areas of the device are flattened; (ii) less rotation of the coil upon deployment; (iii) rapid formation of three dimensional structures upon deployment into a body cavity; and (iv) ability to introduce the coil using a catheter into a body cavity in preferred directions relative to the blood system and aneurysm; all without the necessity of varying the diameter of the wire making up the coil. The devices described herein are useful whether the coils have mechanical or electrolytic detachment links at one or both ends.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a coil" includes a mixture of two or more such devices and the like.

The vaso-occlusive devices described herein are typically formed by winding a wire into a first helix, typically a coil; the first helix is then wound into a secondary form. The secondary form is one which, when ejected from a delivery catheter, forms a three-dimensional shape to substantially fill the body cavity. Desirably, the vaso-occlusive device is of a size and shape suitable for fitting snugly within a vascular cavity (e.g., an aneurysm, or perhaps, a fistula).

Figure 1:
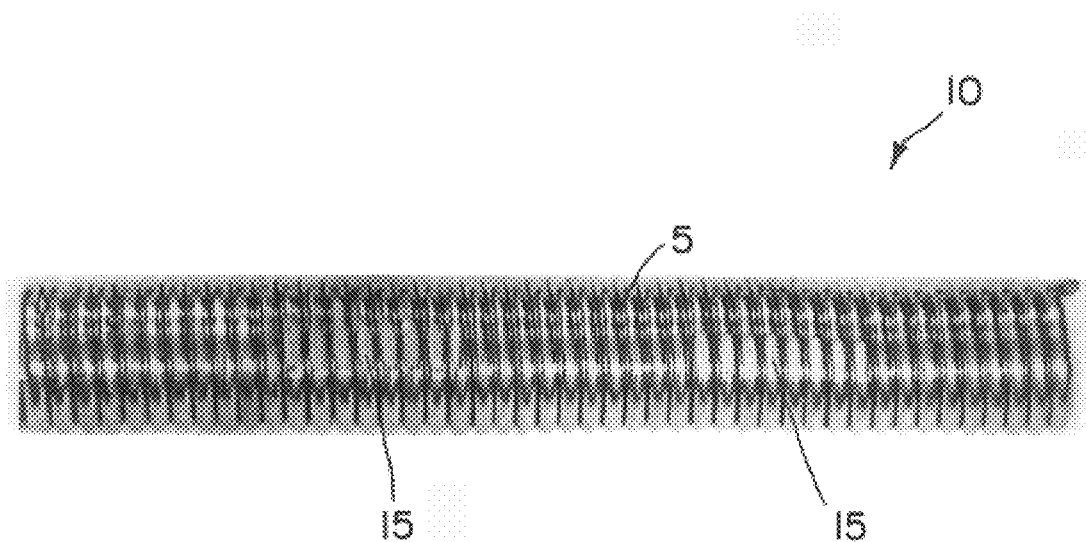
FIG. 1 is a perspective view of one embodiment of the present invention showing a linear coil where portions of the coil along the same axis have been flattened.

FIG. 1 shows one embodiment of the present invention where a wire (5) has been shaped into a linear, helical coil (10) made up of multiple turns of the wire. Portions of the wire making up the individual turns of the primary coil have been flattened (15). Flattened areas may be induced into the linear coil by any number of methods, including but not limited to mechanically swaging, by rolling the primary coil against a high strength (e.g., hard) material such as a mandrel, by crimping the coil or by grinding the coil.

As shown in FIG. 1, the flattened portions of the wire making up the coil are all in the same longitudinal axis (of the primary coil) and all are approximately the same dimensions (e.g., an oval shape on the surface of a single turn of the coil). It will be apparent to those of skill in the art in view of the teachings herein that the wire making up any single turn of the coil can be flattened in one or more areas. It will also be apparent that the wire making up some turns of the coil may not be flattened in any areas. Further, it will also be evident that the flattened areas of the coil may have similar or different shapes and dimensions. In preferred embodiments, less than about 50% of the circumference of the cross-section the wire making up the coil; more preferably, less than about 40%; even more preferably, less than about 30%; even more preferably, less than about 20%; even more preferably, less than about 10% of the circumference of the cross-section of the wire making up the coil of the helically wound coil is flattened. Typically, the flattened areas form a pattern spanning multiple turns of the primary coil, for example the stripe like pattern shown in FIG. 1.

Figure 2:
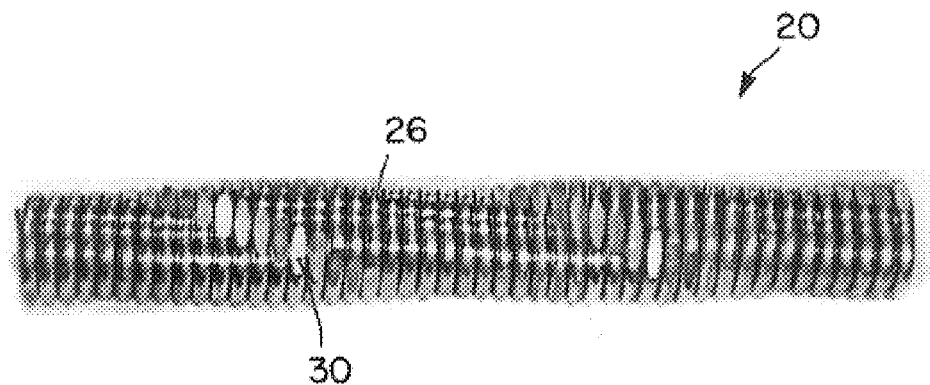
FIG. 2 is a perspective view of one embodiment of the present invention showing a linear coil where portion of the coil along a helical axis have been flattened.
Figure 3:
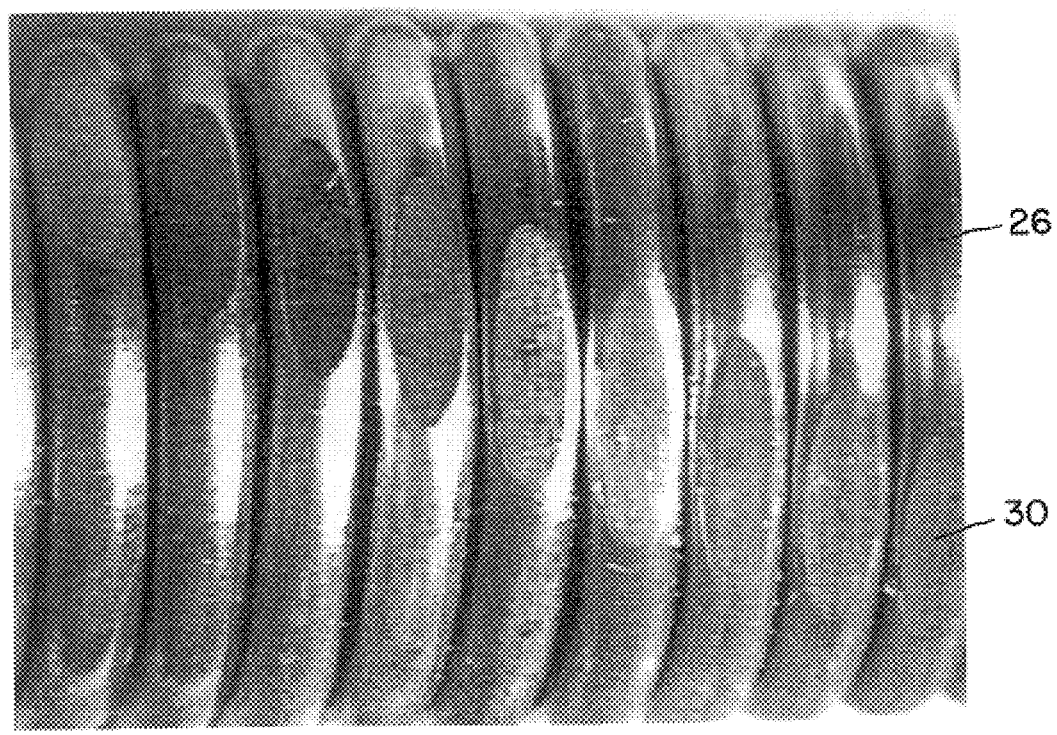
FIG. 3 is a higher magnification view of the embodiment shown in FIG. 2.

FIGS. 2 and 3 depict another embodiment where a wire (26) has been shaped into a primary linear helical coil (20) and portions of the wire making up the coil have been flattened (30). In this embodiment, the flattened portions make a helical (or spiral) pattern along the length of the coil. This pattern is seen in higher magnification in FIG. 3. In other embodiments, the flattened portions make a alternating pattern and in still other embodiments, the flattened portions make a random pattern. The pattern is not crucial, so long as it allows, and preferably, promotes, folding of the coil into a three dimensional structure.

The number and dimensions of the flattened areas in addition to the pattern formed by these areas provide a method of promoting folding of the coil into a three-dimensional structure in certain directions. Thus, depending on the positioning and size of the flattened areas, the coil can be induced to curve in one direction more than the other and, accordingly, can be more easily deployed into a body cavity by the user. In addition, the coils will form three-dimensional structures of differing shapes depending on the size and location of the flattened areas. For example, the swirl or helical pattern of flattening shown in FIGS. 2 and 3 may result in the formation of more random three-dimensional structures as compared to conventional, non-flattened coils. Determining the patterns, size and location to achieve the desired structures is within the purview of the skilled artisan in view of the teachings herein.

In addition to the embodiments depicted in the Figures (where the wire is flattened in one or more areas which are on the exterior surface of the linear coil), the present invention also contemplates embodiments where the interior surface of the linear coil will have flattened areas. This can be achieved in any number of ways, for example, the wire could be flattened prior to winding into a helical coil and, in this way, flattened portions may be found on the interior surface of the primary coil.

Figure 4:
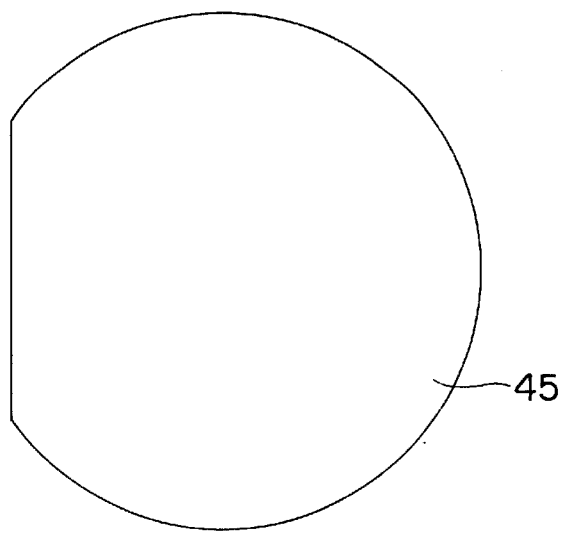
FIG. 4 is a cross-section view of a wire making up one turn of a linear coil where a portion of the linear coil has been flattened in one area.

FIG. 4 is a cross-sectional view of a flattened wire (45) making up the helical linear coil showing that the round cross-section of the wire making up the helical coil is flattened in at least one area to produce a "D" shaped cross section.

Figure 5:
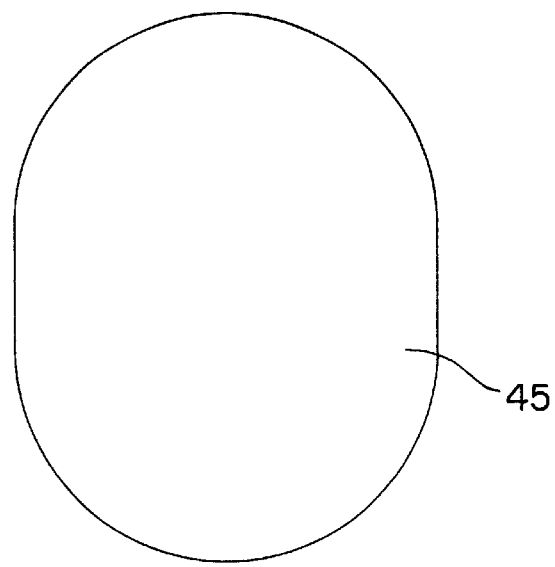
FIG. 5 is another cross-section view of a wire making up one turn of a linear coil where a portion of the linear coil has been flattened in two areas to produce an oval cross-section.

FIG. 5 is a cross-sectional view of a flattened wire (45) making up the helical linear coil showing that the round cross-section of the wire making up the helical coil is flattened in two areas to produce an oval, ribbon shape.

Figure 6:
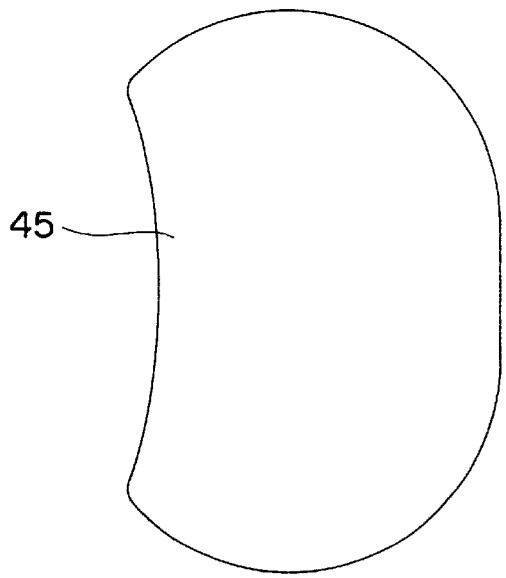
FIG. 6 is another cross-section view of a wire making up one turn of a linear coil where a portion of the linear coil has been flattened in two areas to produce a cross-section where at least one flattened area appears concave.

FIG. 6 is a cross-sectional view of a flattened wire (45) making up the helical linear coil showing that the round cross-section of the wire making up the helical coil is flattened in two areas to produce an oval shape which is concave (e.g., arc-shaped) on one side. Furthermore, it will be apparent that if the wire is flattened in more than one area, the cross-section assume other non-round shapes.

The material used in constructing the vaso-occlusive member (e.g., the wire) may be any of a wide variety of materials; preferably, the wire is a radio-opaque material such as a metal or a polymer. Suitable metals and alloys for the wire making up the primary coil include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire. If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like.

Generally speaking, when the device is formed of a metallic coil and that coil is a platinum alloy or a superelastic alloy such as nitinol, the diameter of the wire used in the production of the coil will be in the range of 0.0005 and 0.006 inches. The wire of such diameter is typically then wound into a primary coil having a primary diameter of between 0.005 and 0.035 inches. For most neurovascular indications, the preferable diameter is 0.010 to 0.018 inches. We have generally found that the wire may be of sufficient diameter to provide a hoop strength to the resulting device sufficient to hold the device in place within the chosen body cavity without distending the wall of the cavity and without moving from the cavity as a result of the repetitive fluid pulsing found in the vascular system.

The axial length of the primary coil will usually fall in the range of 0.5 to 100 cm, more usually 2.0 to 40 cm. Depending upon usage, the coil may well have 100–400 turns per centimeter, preferably 200–300 turns per centimeter. All of the dimensions here are provided only as guidelines and are not critical to the invention. However, only dimensions suitable for use in occluding sites within the human body are included in the scope of this invention.

The overall diameter of the device as deployed is generally between 2 and 20 millimeters. Most aneurysms within the cranial vasculature can be treated by one or more devices having those diameters. Of course, such diameters are not a critical aspect of the invention.

Central to the present invention is flattening certain areas of the primary coil to promote formation of a three-dimensional structure when deployed into a body cavity. Thus, the coil material (e.g., an elongated wire) is first wound into a primary coil as described above using a mandrel which functions as a support for winding and/or annealing. The winding mandrel should be of sufficient heat resistance to allow a moderate annealing step. The mandrel may be made of a refractory material such as glass, alumina or zirconia (for heat-treating devices made of purely metallic components) or may be made of a metallic material (e.g., stainless steel). The pattern of winding and/or flattening on the mandrel provides both the three dimensional shape of the invention at deployment and also determines which areas of the coil are in contact with which areas of the mandrel. The mandrel and attached coil are annealed (e.g., by heating inductively or in a furnace). A typical annealing step for a platinum/tungsten alloy coil would involve a 1100° F. heating step in air for about between about 15–20 minutes to about 6 hours. The primary coil is typically linear after it has been wound and annealed.

Also contemplated in this invention is the attachment of various fibrous materials to the inventive coil for the purpose of adding thrombogenicity to the resulting assembly. The fibrous materials may be attached in a variety of ways. A series of looping fibers may be looped through or tied to coil and continue axially down the coil. Another variation is by tying the tuft to the coil. Tufts may be tied at multiple sites through the coil to provide a vast area of embolus forming sites. The primary coil may be covered by a fibrous braid. The method for producing the former variation is described in U.S. Pat. Nos. 5,226,911 and 5,304,194 to Chee. The method of producing the fibrous braid is described in U.S. Pat. No. 5,382,259, issued Jan. 17, 1995, to Phelps and Van.

The coils described herein can also include additional additives, for example, any material that exhibits biological activity in vivo. Non-limiting examples of suitable bioactive materials are known to those of skill in the art.

The inventive compositions may be associated with other materials, such as radioactive isotopes, bioactive coatings, polymers, fibers, etc., for example by winding, braiding or coating onto the device one or more of these materials, typically prior to introduction into the subject. Methods of associating polymeric materials with a solid substrate such as a coil are known to those of skill in the art, for example as described in U.S. Pat. Nos. 5,522,822 and 5,935,145. In yet other embodiments, the solid substrate itself is made to be radioactive for example using radioactive forms of the substrate material (e.g., metal or polymer). Polymeric or metallic substrates can be made radioactive by known methods such as electrodeposition (see, e.g., Hafeli et al., supra); ion beam deposition (see, e.g., Fehsenfeld, supra), impregnation techniques or the like. Thus, the solid substrates can be made to be radioactive after formation by deposition (e.g., coating, winding or braiding), impregnantion (e.g. ion-beam or electrodeposition) or other techniques of introducing or inducing radioactivity.

The mechanical occlusive devices may include a wide variety of synthetic and natural polymers, such as polyurethanes (including copolymers with soft segments containing esters, ethers and carbonates), ethers, acrylates (including cyanoacrylates), olefins (including polymers and copolymers of ethylene, propylene, butenes, butadiene, styrene, and thermoplastic olefin elastomers), polydimethyl siloxane-based polymers, polyethyleneterephthalate, cross-linked polymers, non-cross linked polymers, rayon, cellulose, cellulose derivatives such nitrocellulose, natural rubbers, polyesters such as lactides, glycolides, caprolactones and their copolymers and acid derivatives, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. In a preferred embodiment, the polymeric filament comprises the materials of the present invention or other suture materials that have already been approved for use in wound heating in humans.

Methods of Use

The flattened coils described above are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the mechanical devices prior to introducing the inventive composition. Shortly after the mechanical devices and the inventive composition are placed within the aneurysm, an emboli begins to form and, at some later time, is at least partially replaced by neovascularized collagenous material formed around the vaso-occlusive devices.

In using the occlusive devices of the present invention, a selected site is reached through the vascular system using a collection of specifically chosen catheters and guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

The mechanical or solid vaso-occlusion device may be used as a kit with the inventive polymeric composition.

Modifications of the procedure and device described above, and the methods of using them in keeping with this invention will be apparent to those having skill in this mechanical and surgical art. These variations are intended to be within the scope of the claims that follow.

What is claimed is:

1. A vaso-occlusive device comprising an elongated wire having a round cross-section wound into a first configuration of a helical linear coil having a longitudinal axis and two ends, wherein the helical linear coil self-forms into a second configuration when deployed into a body cavity and wherein selected portions of the wire wound into the helical linear coil have been flattened such that the cross-section of the wire is not round.

2. The vaso-occlusive device of claim 1, wherein the flattened portions of the wire form a pattern over the longitudinal axis of the coil.

3. The vaso-occlusive device of claim 2, wherein the pattern is a striped pattern.

4. The vaso-occlusive device of claim 2, wherein the pattern is a helical pattern.

5. The vaso-occlusive device of claim 2, wherein the pattern is random.

6. The vaso-occlusive device of claim 1, further comprising additional filamentary material attached to the coil.

7. The vaso-occlusive device of claim 1, further comprising a deployment tip attached to at least one of the two ends of the coil.

8. The vaso-occlusive device of claim 7, wherein the deployment tip comprises a mechanically detachable end adapted to attach and detach from a pusher.

9. The vaso-occlusive device of claim 7, wherein the deployment tip comprises an electrolytically detachable end adapted to detach from a pusher by imposition of a current on the pusher.

10. The vaso-occlusive device of claim 1 produced by rolling the linear coil against a high strength material.

11. The vaso-occlusive device of claim 10, wherein the high strength material is a mandrel.

12. The vaso-occlusive device of claim 1 produced by using a swage on the linear coil.

13. A method of occluding a body cavity comprising introducing a vaso-occlusive device according to claim 1 into the body cavity.

14. The method of claim 13, wherein the body cavity is an aneurysm.

* * * * *